(12) United States Patent
Walak et al.

(10) Patent No.: US 6,872,217 B2
(45) Date of Patent: Mar. 29, 2005

(54) RECOILABLE THROMBOSIS FILTERING DEVICE AND METHOD

(75) Inventors: Steven E. Walak, Natick, MA (US); Bernedette Proskoczilo, Cortland, NY (US); Kristian DiMatteo, Maynard, MA (US); Robert B. DeVries, Marlborough, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/350,235

(22) Filed: Jan. 23, 2003

(65) Prior Publication Data

US 2003/0109897 A1 Jun. 12, 2003

Related U.S. Application Data

(63) Continuation of application No. 09/500,209, filed on Feb. 8, 2000, now Pat. No. 6,540,767.

(51) Int. Cl.$^7$ .............................................. A61B 17/00
(52) U.S. Cl. ...................................................... 606/200
(58) Field of Search ................................ 606/200, 127, 606/113, 108, 194; 623/1.1

(56) References Cited

U.S. PATENT DOCUMENTS

| | | | |
|---|---|---|---|
| 3,174,851 A | | 3/1965 | Buehler et al. |
| 3,868,956 A | | 3/1975 | Alfidi et al. |
| 4,425,908 A | | 1/1984 | Simon |
| 4,512,338 A | * | 4/1985 | Balko et al. ............... 606/108 |
| 4,619,246 A | | 10/1986 | Molgaard-Nielsen et al. |
| 4,643,184 A | | 2/1987 | Mobin-Uddin |
| 4,665,906 A | | 5/1987 | Jervis |
| 4,688,553 A | | 8/1987 | Metals |
| 4,727,873 A | | 3/1988 | Mobin-Uddin |
| 4,781,177 A | | 11/1988 | Lebigot |
| 4,817,600 A | | 4/1989 | Herms et al. |
| 4,832,055 A | | 5/1989 | Palestrant |
| 4,990,156 A | | 2/1991 | Lefebvre |
| 5,059,205 A | | 10/1991 | El-Nounou et al. |
| 5,067,957 A | | 11/1991 | Jervis |
| 5,071,407 A | | 12/1991 | Termin et al. |
| 5,108,418 A | | 4/1992 | Lefebvre |
| 5,147,379 A | | 9/1992 | Sabbaghian et al. |
| 5,217,484 A | | 6/1993 | Marks |
| 5,234,458 A | | 8/1993 | Metais |
| 5,242,462 A | | 9/1993 | El-Nounou et al. |
| 5,324,304 A | | 6/1994 | Rasmussen |
| 5,329,942 A | | 7/1994 | Gunther et al. |
| 5,350,398 A | | 9/1994 | Pavcnik et al. |
| 5,370,657 A | | 12/1994 | Irie |
| 5,421,832 A | | 6/1995 | Lefebvre |
| 5,540,712 A | | 7/1996 | Kleshinski et al. |
| 5,601,595 A | | 2/1997 | Smith |
| 5,634,942 A | | 6/1997 | Chevillon et al. |
| 5,649,953 A | | 7/1997 | Lefebvre |
| 5,669,933 A | | 9/1997 | Simon et al. |
| 5,681,347 A | | 10/1997 | Cathcart et al. |
| 5,709,704 A | | 1/1998 | Nott et al. |
| 5,720,764 A | | 2/1998 | Naderlinger |

(Continued)

FOREIGN PATENT DOCUMENTS

| | | |
|---|---|---|
| WO | WP 0025252 | 11/1998 |
| WO | WO 01/15630 A1 | 9/2000 |

*Primary Examiner*—Anhtuan T. Nguyen
*Assistant Examiner*—Tan-Uyen T. Ho
(74) *Attorney, Agent, or Firm*—Crompton, Seager & Tufte LLC (57) ABSTRACT

A thrombosis filter which can be securely affixed at a selected location in the vascular system of a patient and removed when no longer required. An embodiment of the thrombosis filter includes a plurality of struts formed of a shape memory material. A change in temperature can cause the struts to extend and engage a wall of a blood vessel.

3 Claims, 11 Drawing Sheets

U.S. PATENT DOCUMENTS

| | | |
|---|---|---|
| 5,755,778 A | 5/1998 | Kleshinski |
| 5,776,162 A | 7/1998 | Kleshinski |
| 5,810,874 A | 9/1998 | Lefebvre |
| 5,836,968 A | 11/1998 | Simon et al. |
| 5,836,969 A | 11/1998 | Kim et al. |
| 5,976,172 A | 11/1999 | Homsma et al. |
| 6,007,558 A | 12/1999 | Ravenscroft et al. |
| 6,013,093 A | 1/2000 | Nott et al. |
| 6,258,026 B1 | 7/2001 | Ravenscroft et al. |
| 6,267,776 B1 | 7/2001 | O'Connell |
| 6,273,900 B1 | 8/2001 | Nott et al. |
| 6,273,901 B1 | 8/2001 | Whitcher et al. |
| 6,361,545 B1 * | 3/2002 | Macoviak et al. .......... 606/200 |
| 6,391,045 B1 | 5/2002 | Kim et al. |

* cited by examiner

Fig. 17

RECOILABLE THROMBOSIS FILTERING DEVICE AND METHOD

This is a continuation of Application Ser. No. 09/500,209, filed Feb. 8, 2000, now U.S. Pat. No. 6,540,767.

FIELD OF THE INVENTION

The present invention relates generally to filters for use inside blood vessels. More particularly, the present invention relates to thrombus filters which can be securely affixed at a selected location in the vascular system and removed when no longer required.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

SUMMARY OF THE INVENTION

The present invention pertains to a thrombosis filter which can be securely affixed at a selected location in the vascular system of a patient and removed when no longer required. In a first embodiment, the thrombosis filter includes a strut formation, a wire formation, and a body portion. The body portion includes a plurality of apertures. The strut formation includes a plurality of struts each having a fixed end and a free end. The fixed ends of the struts are each fixably attached to the body portion of the thrombus filter inside the apertures; one strut radiating from each aperture.

The wire formation is comprised of a plurality of wires. Each wire has a fixed end and a free end. The fixed ends of the wires are fixably attached to the body portion of the thrombus filter. The struts radiate away from the proximal end of the body portion in a proximal direction such that the strut formation is generally conical in shape. Likewise, the wires radiate away from the distal end of the body portion in a distal direction such that the wire formation is generally conical in shape.

When the thrombosis filter is disposed in a blood vessel, the wire formation acts to capture blood clots. The generally conical shape of the wire formation serves to urge captured blood clots toward the center of the blood flow. The flow of blood around the captured clots allows the body's natural lysing process to dissolve the clots. The struts are formed of a shape memory material. At about body temperature, the struts assume an extended shape and engage the walls of the blood vessel. At a selected temperature, other than body temperature, the struts assume a contracted shape. This contracted shape causes the struts to contract inside the apertures of the body portion.

Various techniques can be used to alter the temperature of the struts causing them to retract. Suitable techniques for warming the thrombosis filter include applying electromagnetic energy to a portion of the thrombosis filter (e.g. laser light delivered by an optical fiber), and inducing an electrical current through a portion of the thrombosis filter. In a preferred embodiment, the struts are cooled by introducing a relatively cool fluid into the blood vessel proximate the thrombosis filter. After the struts are retracted, the thrombosis filter can be readily pulled into the lumen of a removal catheter.

A second embodiment of the thrombosis filter includes a generally cylindrical anchoring portion and a generally conical filtering portion terminating at a body member. The filtering portion includes a plurality of elongated strands. The strands of the filtering portion are arranged in an interwoven pattern to create cells. The interwoven pattern of strands enables the filtering portion to trap or capture blood clots. The conical shape of the filtering portion urges captured blood clots toward the center of the blood flow. The flow of blood around the captured blood clots allows the body's natural lysing process to dissolve the clots.

The strands extend beyond the filtering portion to create the anchoring portion. The strands are formed from a shape memory alloy. The shape memory alloy construction of the thrombosis filter allows it to change shape in response to a change in temperature. At about body temperature, the thrombosis filter assumes an extended shape. At a selected temperature other than body temperature, the thrombosis filter assumes a contracted shape. When the thrombosis filter assumes a contracted shape the anchor portion of the thrombosis filter disengages the walls of the blood vessel. When it is desirable for the thrombosis filter to be removed from a blood vessel, a physician may selectively heat or cool the thrombosis filter causing it to assume the contracted shape. Various techniques can be used to change the temperature of the thrombosis filter. In a preferred embodiment, the thrombosis filter is cooled by introducing a relatively cold fluid into the blood vessel proximate the thrombosis filter. Once the thrombosis filter assumes a contracted shape, it may be pulled in the lumen of a removal catheter.

DETAILED DESCRIPTION OF THE INVENTION

The following detailed description should be read with reference to the drawings, in which like elements in different drawings are numbered identically. The drawings which are not-necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
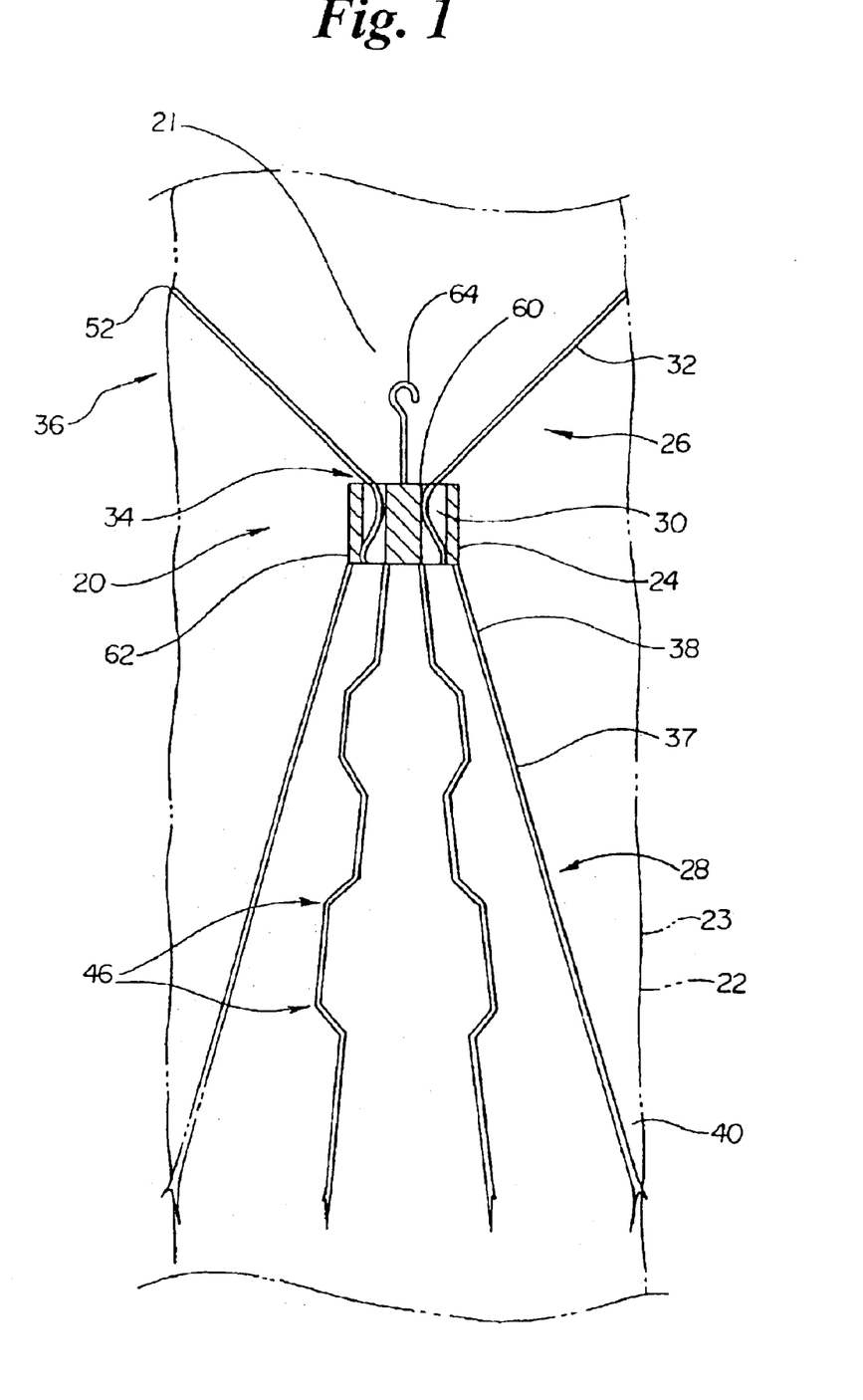
FIG. 1 is a plan view of a thrombus filter with struts in an extended position.

Reference is now made to the drawings, in which like numbers refer to like elements throughout. FIG. 1 is a plan view of a thrombosis filter 20 positioned in a lumen 21 of a blood vessel 22. Blood vessel 22 includes walls 23 which define lumen 21. The main components of thrombosis filter 20 are a body portion 24, a strut formation 26 and a wire formation 28.

Body portion 24 includes a plurality of apertures 30. Strut formation 26 includes a plurality of struts 32 each having a fixed end 34, and a free end 36. Fixed ends 34 of struts 32 are each fixedly attached to body portion 24 inside apertures 30; one strut 32 radiating from each aperture 30.

Wire formation 28 is comprised of a plurality of wires 37. Each wire 37 has a fixed end 38 and a free end 40. Fixed ends 38 of wires 37 are fixedly attached to body portion 24.

Wire 37 may include a plurality of bends 46 disposed between free end 40 and fixed end 38. Free end 40 of each wire 37 includes an anchor 50. Likewise, each strut 32 includes an anchor 52. In FIG. 1, anchors 50 and 52 are pictured as sharp projections or barbs. It should be understood that anchors 50 and 52 may be comprised of other means for anchoring without departing from the spirit or scope of this invention.

Body portion 24 includes a proximal end 60 and a distal end 62. A coupling member 64 is fixedly attached to proximal end 60 of body portion 24.

Struts 32 radiate away from proximal end 60 of body portion 24 in a proximal direction. Such that strut formation 26 is generally conical in shape. Likewise, wires 37 radiate away from distal end 62 of body portion 24 in a distal direction such that wire formation 28 is generally conical in shape.

When thrombosis filter 20 is disposed in a blood vessel, wire formation 28 acts to trap, or capture blood clots. The generally conical shape of wire formation 28 serves to urge captured blood clots toward the center of the blood flow. The flow of blood around the captured blood clots allows the body's natural lysing process to dissolve the clots.

Struts 32 act as opposing wall contacting members and serve to position thrombosis filter 20 in the center of lumen 21 of blood vessel 22 shown with hidden lines in FIG. 1. Likewise, wires 37 act as opposing wall contacting members and serve to position thrombosis filter 20 in the center of lumen 21 of blood vessel 22. Anchors 52 of struts 32 generally oppose anchors 50 of wires 37. These opposing anchors 50 and 52 serve to maintain the position of thrombosis filter 20, preventing it from migrating upstream or downstream in blood vessel 22. In the embodiment shown in FIG. 1 anchors 50 and 52 include a plurality of sharp projections which penetrate the walls of blood vessel 22.

Struts 32 and wires 37 may all be fabricated from wire with a circular, rectangular or other cross section. For example, straight wires 37 may be comprised of 0.018" diameter wire. Stainless steel, titanium, and nickel titanium alloy have all been found to be acceptable materials for wires 37.

Struts 32 are formed from a shape-memory material. The shape-memory material of struts 32 may be a shape-memory polymer, or a shape-memory alloy. Suitable shape memory materials are commercially available from Memry Technologies (Brookfield, Conn.), TiNi Alloy Company (San Leandro, Calif.), and Shape Memory Applications (Sunnyvale, Calif.). In a preferred embodiment, struts 32 are comprised of an alloy of titanium and nickel known in the art as Nitinol.

The shape-memory material construction of struts 32 enable struts 32 to change shape in response to a change in temperature. At about body temperature, struts 32 assume an extended shape as shown in FIG. 1. At a selected temperature other than body temperature, struts 32 assume a contracted shape as shown in FIG. 2.

Figure 2:
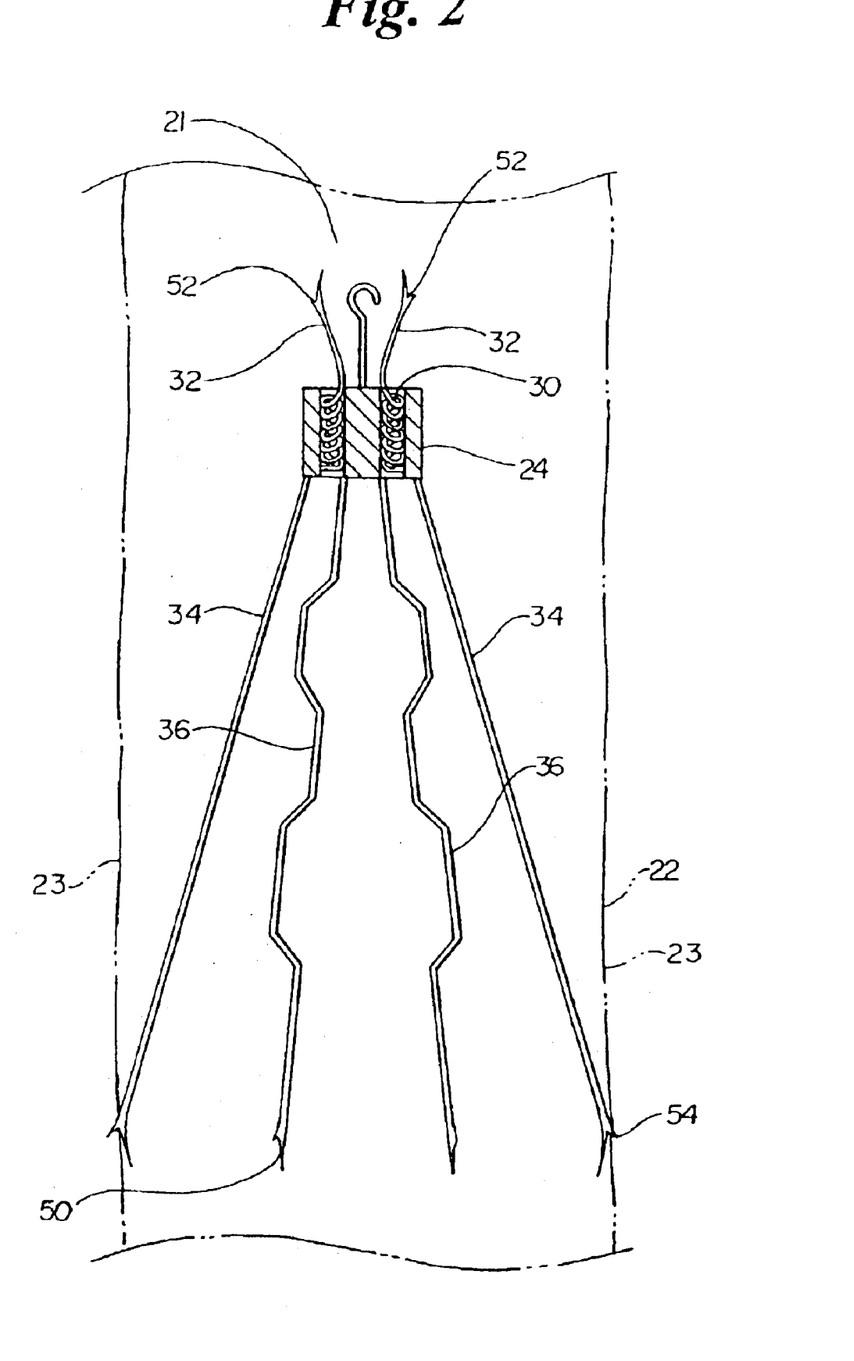
FIG. 2 is a plan view of a thrombus filter with struts in a contracted position.

In FIG. 2, struts 32 have partially contracted inside apertures 30 of body portion to 24. As a result of the contraction of struts 32, anchors 52 have retracted from walls 23 of blood vessel 22.

Various techniques can be used to alter the temperature of struts 32. Suitable techniques for warming struts 32 include applying electromagnetic energy to body portion 24 (e.g. laser light delivered by an optical fiber), and applying electrical energy to thrombosis filter 20 (e.g. inducing a current through struts 32).

Figure 3:
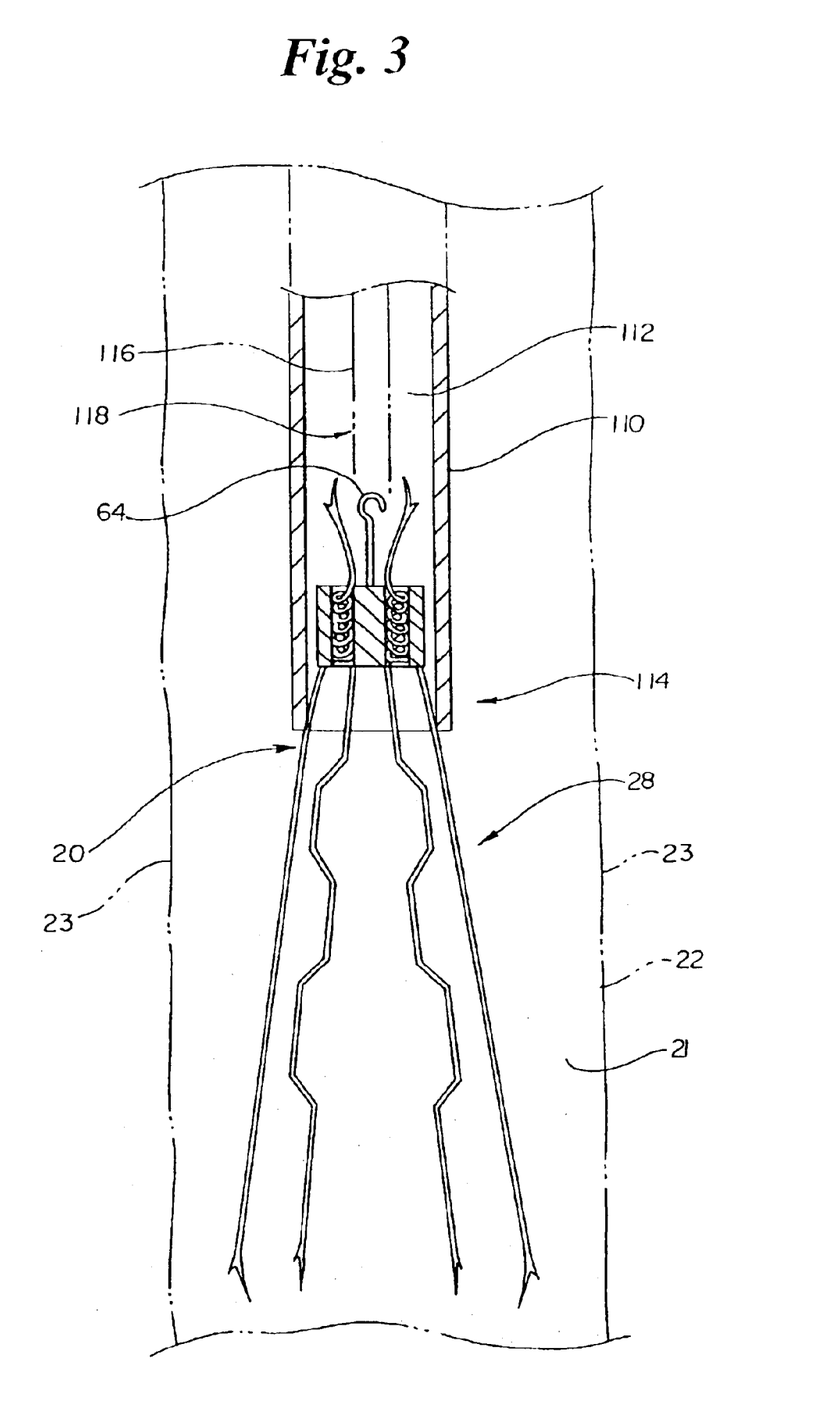
FIG. 3 is a plan view illustrating the removal of a thrombus filter from a blood vessel.

A process which may be used to remove thrombosis filter 20 from lumen 21 of blood vessel 22 is illustrated in FIG. 3. A removal catheter 110 with a lumen 112 and a distal end 114 is disposed in lumen 21 of blood vessel 22. Removal catheter 10 enters the patients vascular system at a point which is readily accessible to the physician. Once in the vascular system, removal catheter 110 is urged forward until distal end 114 is proximate thrombosis filter 20. For example, if thrombosis filter 20 is located in the inferior vena cava of a patients vascular system, removal catheter 110 may enter the vascular system at the femoral vein. Alternately, if thrombosis filter 20 is located in the superior vena cava of a patients vascular system, removal catheter 110 may enter the vascular system at the jugular vein. In either case, the filter removal procedure is minimally invasive, and does not require general anesthesia.

An elongated retrieval member 116 including a distal end 118 and a proximal end 120 (not shown) is disposed in lumen 112 of removal catheter 110. In FIG. 3, distal end 118 of retrieval member 116 has been releasibly mated to coupling member 64 of thrombosis filter 20. Proximal end 120 of elongated retrieval member 116 protrudes beyond the proximal end of removal catheter 110. Both removal catheter 110 and retrieval member 116 extend outside the body of the patient.

When distal end 114 of removal catheter 110 reaches a position proximate thrombosis filter 20, the temperature of struts 32 is altered, causing them to retract. With struts 32 in a retracted position, thrombosis filter 20 may be readily pulled into lumen 112 of removal catheter 110 by applying a pulling force to proximal end 120 of retrieval member 116. This pulling force is transferred via retrieval member 116 to thrombosis filter 20. The pulling force applied to retrieval member 116 of thrombosis filter 20 pulls anchors 50 of wires 37 out of blood vessel 22.

As shown if FIG. 3, pulling thrombosis filter 20 into lumen 112 of removal catheter 110 causes wires 37 to collapse causing wire formation 28 to transform from a generally conical shape toward a generally cylindrical shape. With wires 37 in a collapsed position, thrombosis filter 20 may be pulled completely into lumen 112 of removal catheter 110. Once thrombosis filter 20 is inside lumen 112; removal catheter 110 may be withdrawn from blood vessel 22.

Figure 4:
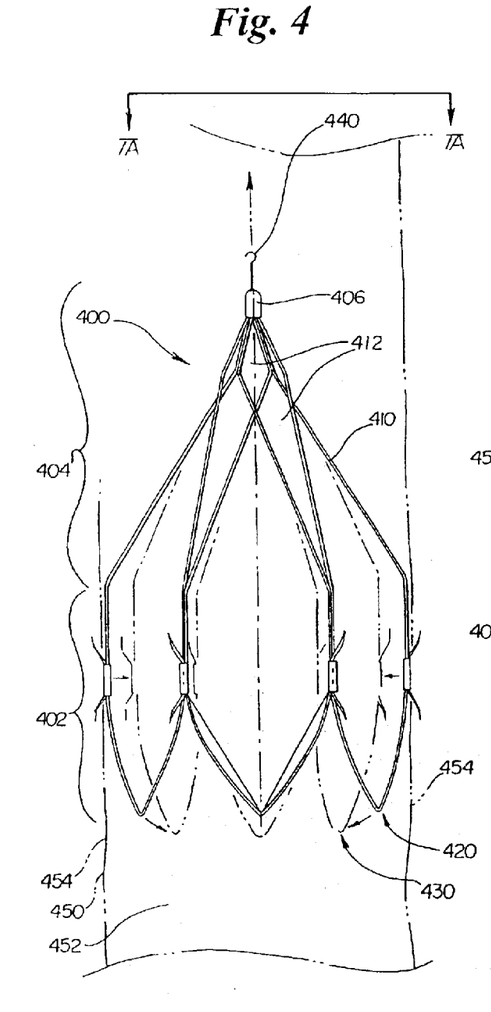
FIG. 4 is a plan view of an alternate embodiment of a thrombus filter.

FIG. 4 is a plan view of a second embodiment of a thrombosis filter 400, disposed in a blood vessel 450. Blood vessel 450 includes a lumen 452 defined by blood vessel walls 454. Thrombosis filter 400 includes a generally cylindrical anchoring portion 402, and a generally conical filtering portion 404 terminating at a body member 406. Filtering portion 404 includes a plurality of elongated struts or strands 410. Strands 410 of filtering portion 404 are arranged in an interwoven pattern to create cells 412. The interwoven pattern of strands 410 enables filtering portion 404 to trap, or capture blood clots. The conical shape of filtering, portion 404 urges captured blood clots toward the center of the blood flow. The flow of blood around the captured blood clots allows the to body's natural lysing process to dissolve the clots.

Strands 410 extend beyond filtering portion 404 into anchoring portion 402. Strands 410 are formed from a shape-memory material. The shape-memory material of strands 410 may be a shape-memory polymer or a shape memory metal. Suitable shape memory materials are commercially available from Memry Technologies (Brookfield, Conn.), TiNi Alloy Company (San Leandro, Calif.), and Shape Memory Applications (Sunnyvale, Calif.). In a preferred embodiment, strands 410 are comprised of an alloy of titanium and nickel known in the art as Nitinol.

The term "strands", as used in describing strands 410 should not be mistaken as limiting strands 410 to elements having a circular cross section. The cross section of strands 410 may be any number of shapes. For example, the cross section of strands 410 could be rectangular, elliptical, etc. Embodiments of the present invention have been envisioned in which strands 410 are comprised of laser cut elements.

The shape-memory alloy construction of strands 410 enable thrombosis filter 400 to change shape in response to a chance in temperature. In FIG. 4, thrombosis filter 400 is shown in an extended shape 420. Thrombosis filter 400 assumes extended shape 420 when strands 410 are generally at about body temperature. A contracted shape 430 is shown with phantom lines in FIG. 4. Thrombosis filter 400 assumes contracted shape 430 when strands 410 are at a selected temperature other than body temperature.

When it is desirable for thrombosis filter 400 to be removed from a blood vessel, a physician may selectively heat or cool thrombosis filter 400 causing it to assume contracted shape 430. When thrombosis filter 400 assumes contracted shape 430, anchoring portion 402 retracts away from walls 454 of blood vessel 450.

Various techniques may be utilized to change the temperature of thrombosis filter 400. Suitable techniques for warming thrombosis filter 400 include applying electromagnetic energy to body member 406 (e.g. laser light delivered by an optical fiber), and applying electrical energy to thrombosis filter 400 (e.g. inducing a current through strands 410). In a preferred cooling method, the thrombosis filter is cooled by introducing a relatively cold fluid into the body proximate the thrombosis filter.

Thrombosis filter 400 may be removed from lumen 452 of blood vessel 450 utilizing a method similar to the one described for the previous embodiment. A removal catheter is positioned in lumen 452 of blood vessel 450 so that the distal end of the removal catheter is proximate thrombosis filter 400.

Embodiments of the present invention are possible in which portions of the thrombosis filter are coated with a coating material. Embodiment of the present invention have been envisioned in which the coating material prevents tissue growth proximate the filter to facilitate subsequent disengagement of the filter. Embodiment of the present invention have also been envisioned in which the coating material comprises a non-stick material to facilitate subsequent disengagement of the filter. These envisioned coating materials may be utilized with the various embodiments disclosed herein.

The removal catheter may enter the patients vascular system at a point which is readily accessible to the physician. Once in the vascular system, the removal catheter is urged forward until its distal end is proximate thrombosis filter 400. For example, if thrombosis filter 400 is located in the inferior vena cava of a patients vascular system, the removal catheter may enter the vascular system at the femoral vein. Alternately, if thrombosis filter 400 is located in the superior vena cava of a patients vascular system, the removal catheter may enter the vascular system at the jugular vein. In either case, the filter removal procedure is minimally invasive, and usually does not require general anesthesia.

An elongated retrieval member is disposed in the lumen of the retrieval catheter. The distal end of the elongated retrieval member is releasably mated to a coupling member 440 which is fixedly attached to body member 406 of thrombosis filter 400.

A presently preferred method includes the step of altering the temperature of strands 410. When the temperature of strands 410 is altered, they change shape, causing thrombosis filter 400 to retract from extended position 420 to contracted position 430. The change in shape causes anchor portion 402 to disengage walls 454 of blood vessel 450

With anchor portion 402 disengaged from walls 454 of blood vessel 450, thrombosis filter 400 may be readily pulled into the lumen of the retrieval catheter. The pulling force is applied to thrombosis filter 400 by pulling on the proximal end of the elongated retrieval member which has been joined to coupling member 440.

Figure 5:
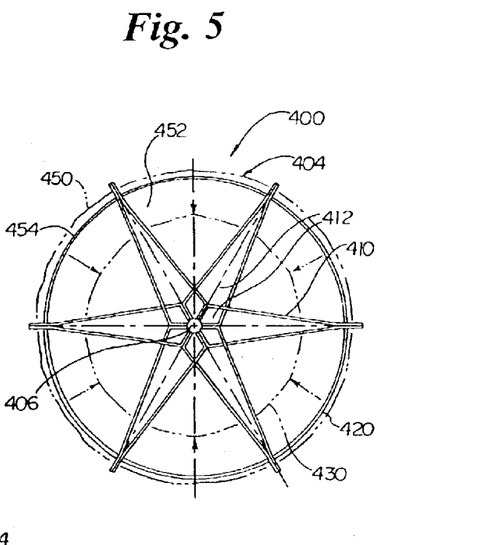
FIG. 5 is a plan view of the thrombus filter of FIG. 4.

FIG. 5 is a plan view illustrating thrombosis filter 400 taken from line A—A shown in FIG. 4. Thrombosis filter 400 is disposed in lumen 452 of blood vessel 450. Thrombosis filter 400 includes filtering portion 404. Filtering portion 404 includes strands 410 which are arranged in an interwoven pattern to create cells 412. The interwoven pattern of strands 410 enables filtering portion 404 to trap, or capture blood clots. The conical shape of filtering portion 404 urges captured blood clots toward the center of the blood flow. The flow of blood around the captured blood clots allows the body's natural lysing process to dissolve the clots.

Figure 6:
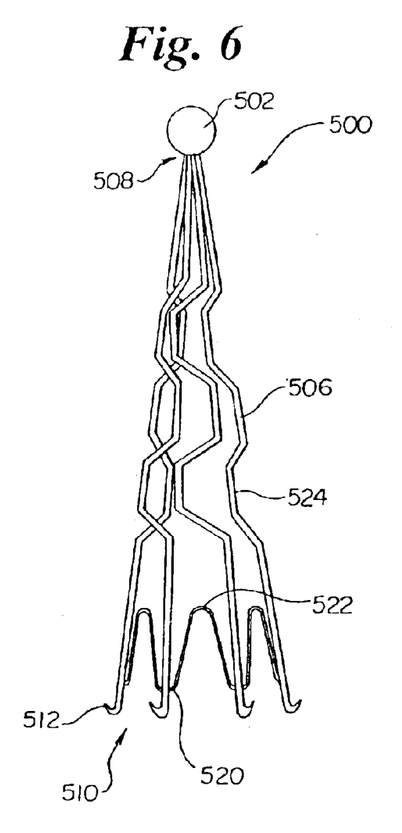
FIG. 6 is a plan view of an additional embodiment of a thrombosis filter in accordance with the present invention.

FIG. 6 is a plan view of an additional embodiment of a thrombosis filter 500. In the embodiment of FIG. 6, thrombus filter 500 includes a body portion 502 and a plurality of spokes 506. Spokes 506 each have a joined end 508 and a free end. 510. Joined end 508 of each spoke 506 is fixedly attached to body portion 502. Spokes 506 radiate outwardly from body portion 502 such that thrombus filter 500 is generally conical in shape. An anchor member 512 is disposed proximate the free end 510 of each spoke 506.

Thrombosis filter 500 also includes a ring 520 which is disposed proximate free ends 510 of spokes 506. In the embodiment of FIG. 6, each spoke 506 is fixed to ring 520. Those of skill in the art will appreciate that many methods may be used to fix ring 520 to Spokes 506. Examples of methods which may be Suitable in some applications include welding, brazing, soldering, and the use of adhesives. Other embodiments of thrombus filter 500 are possible, in which ring 520 mechanically engages spokes 506. For example, spokes 506 may include holes, slots, or eyes. In this exemplary embodiment, ring 520 may be threaded through the holes, slots, or eyes of spokes 506.

As shown in FIG. 6, ring 520 of thrombus filter 500 includes a plurality of bends 522. In a presently preferred embodiment, ring 520 is comprised of a shape memory alloy. Suitable shape memory alloys are commercially available from Memry Technologies (Brookfield, Conn.), TiNi Alloy Company (San Leandro, Calif.), and Shape Memory Applications (Sunnyvale, Calif.). In a presently most preferred embodiment, ring 520 is comprised of an alloy of titanium and nickel known in the art as Nitinol.

When thrombus filter 500 is released in a blood vessel, spokes 506 expand outward so that free ends 510 of spokes 506 contact the walls of the blood vessel. The geometry of anchor members 512 results in localized contact between the thrombus filter and the blood vessel walls. Anchor members 512 become imbedded in the walls of the blood vessel proximate these points of initial contact.

Figure 7:
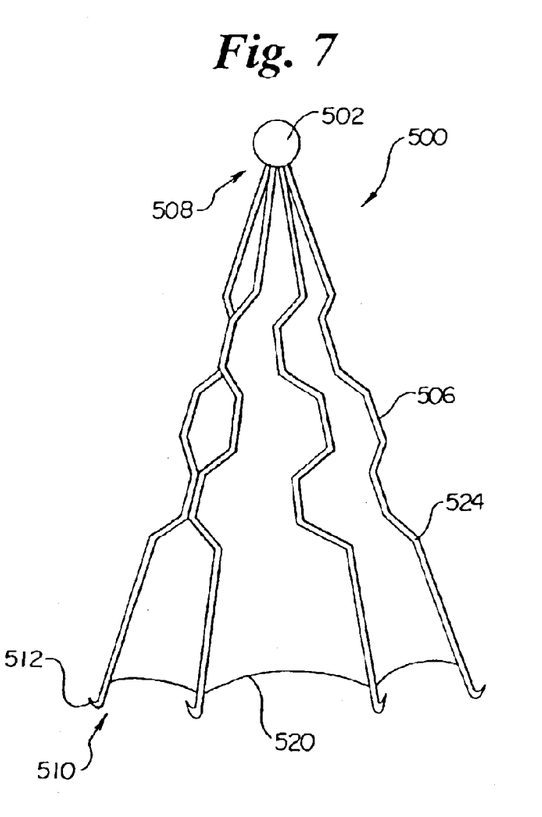
FIG. 7 is a plan view of the thrombus filter of FIG. 6 in an expanded state.

FIG. 7 is a plan view of a thrombus filter 500 in an expanded state. Thrombus filter 500 of the embodiment shown in FIGS. 6 and 7 includes an insulating layer 524 substantially covering thrombus filter 500 including body portion 502, spokes 506, and anchor members 512. A number of materials have been found to be suitable for use in insulating layer 524, these materials include fluoropolytetrafluoroethylene (PTFE), polyethylene (PE), polypropylene (PP), polyvinylchloride (PVC), and polyurethane. A number of manufacturing processes may be used to create insulating layer 524. For example, a portion of insulating layer 524 may be made up of sections of shrink tubing. The shrink tubing sections may be positioned over the spokes then shrunk by the application of heat. A spray process may also be used to apply insulating layer 524 to thrombus filter 500. For example, spraying PTFE solids in a suitable solvent carrier is a process which has been found suitable for this application.

Another material which may be used to fabricate insulating layer 524 is a thermoplastic generically known as parylene. There are a variety of polymers based on para-xylylene. These polymers are typically placed onto a substrate by vapor phase polymerization of the monomer. Parylene N coatings are produced by vaporization of a di(P-xylylene)dimer, pyrollization, and condensation of the vapor to produce a polymer that is maintained at comparatively lower temperature. In addition to parylene-N, parylene-C is derived from di(monochloro-P-xylylene) and parylene-D is derived from di(dichloro-P-xylylene). There are a variety of known ways to apply parylene to substrates.

It should be understood that insulating layer 524 may include apertures, when these apertures are necessary to create an electrical circuit. The significance of these apertures and insulating layer 524 will be made clear in the discussion which follows.

Figure 8:
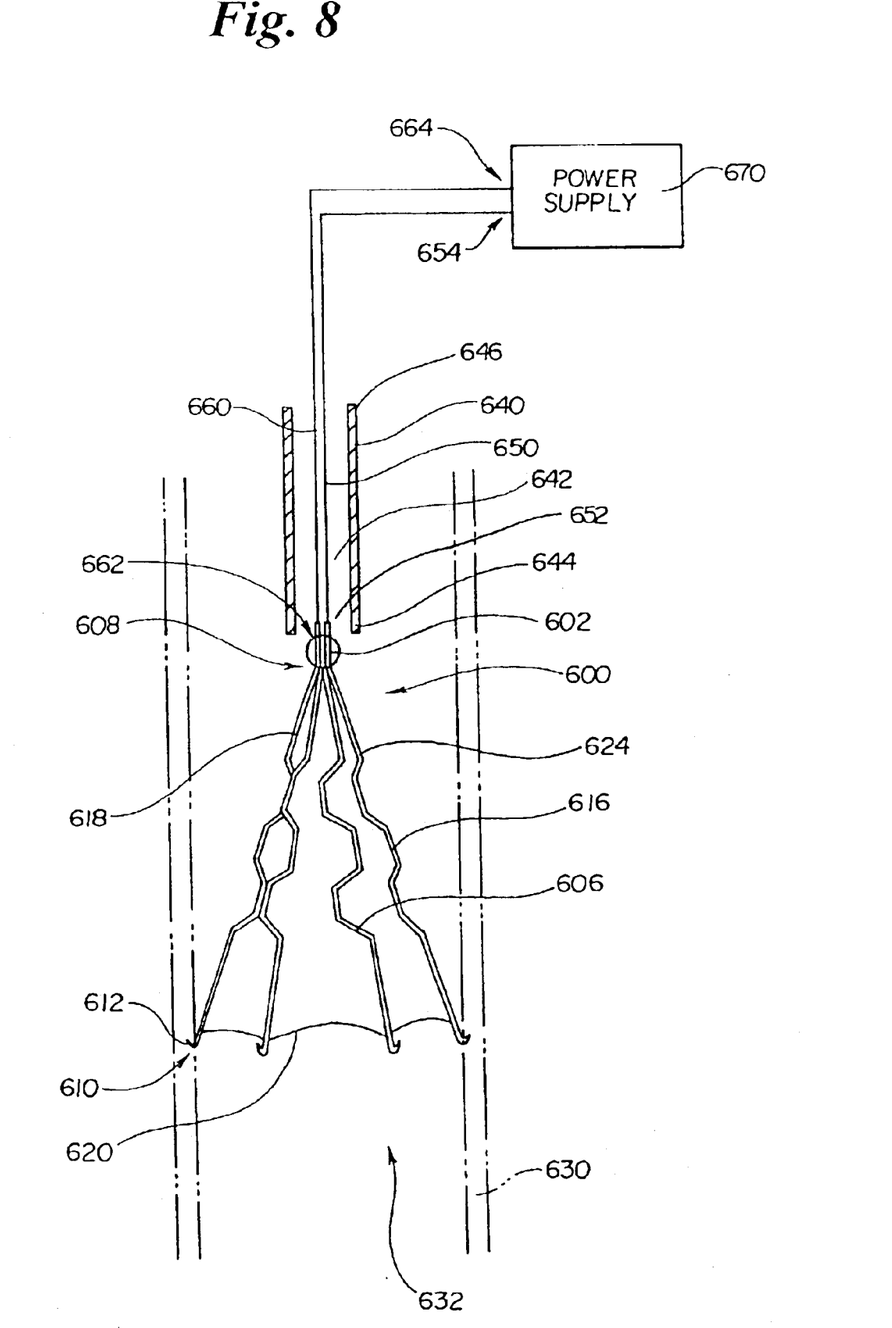
FIG. 8 is a diagrammatic view illustrating a process which may be used to remove a thrombus filter from the body of a patient, the diagrammatic view including an exemplary embodiment of a thrombus filter, and an exemplary embodiment of a removal catheter.

FIG. 8 is a diagrammatic view illustrating a process which may be used to remove a thrombus filter 600 from the body of a patient. In the embodiment of FIG. 7, thrombus filter 600 includes a body portion 602 and a plurality of spokes 606. Spokes 606 each have a joined end 608 and a free end 610. Joined end 608 of each spoke 606 is fixedly attached to body portion 602. In a presently preferred embodiment, body portion 602 is comprised of a non-conductive material so that body portion 602 does not form a path for electric current between spokes 606.

Thrombosis filter 600 also includes a ring 620 which is disposed proximate free ends 610 of spokes 606. In a presently preferred embodiment, ring 620 is electrically coupled to spokes 606. Also in a presently preferred embodiment, ring 620 is comprised of a shape memory alloy. Suitable shape memory alloys are commercially available from Memry Technologies (Brookfield, Conn.), TiNi Alloy Company (San Leandro, Calif.), and Shape Memory Applications (Sunnyvale, Calif.). In a presently most preferred embodiment, ring 620 is comprised of an alloy of titanium and nickel known in the art as Nitinol.

In FIG. 8, thrombus filter 600 is disposed within a lumen 632 of a blood vessel 630. A removal catheter 640 is also disposed within lumen 632 of blood vessel 630. A distal end 644 of removal catheter 640 is disposed proximate thrombus filter 600. Removal catheter also includes a lumen 642 and a proximal end 646.

A first electrical conductor 650 and a second electrical conductor 660 are disposed inside lumen 642 of removal catheter 640. First electrical conductor 650 includes a proximal end 654 and a distal end 652. Second electrical conductor 660 includes a proximal end 664 and a distal end 662.

As in the previous embodiment, thrombus filter 600 includes a insulating layer 624. In the embodiment of FIG. 8, distal end 652 of first electrical conductor 650 has penetrated insulating layer 624 of thrombus filter 600 to form an electrical connection with a first spoke 616. Likewise, distal end 662 of second electrical conductor 660 has penetrated insulating layer 624 of thrombus filter 600 to form an electrical connection with a second-spoke 618.

A number of methods may be suitable for forming the electrical connection between the distal ends of the electrical conductors and the spokes. For example, a needle electrode may be disposed at distal ends 652, 662 of electrical conductors 650, 660 respectively. The needle electrodes could penetrate insulating layer 524 and make electrical contact with the spokes. An easily deformable material such as silicone rubber or foam rubber could be disposed around the needle electrode to insulate the electrical connection.

Proximal end 654 of first electrical conductor 650 and proximal end 664 of second electrical conductor 660 are both electrically coupled to a power supply 670. Power supply 670 is used to selectively apply a voltage differential between first electrical conductor 650 and second electrical conductor 660.

In the embodiment of FIG. 8, a circuit path between first spoke 616 and second spoke 618 comprises ring 620. In a presently preferred embodiment, current must travel through ring 620 in order to pass from first spoke 616 to second spoke 618. The voltage differential created by power supply 670 induces a current flow through ring 620. The flow of current through ring 620 causes the temperature of ring 620 to be altered. When the temperature of ring 620 is altered, ring 620 assumes a contracted position as shown in FIG. 9.

Figure 9:
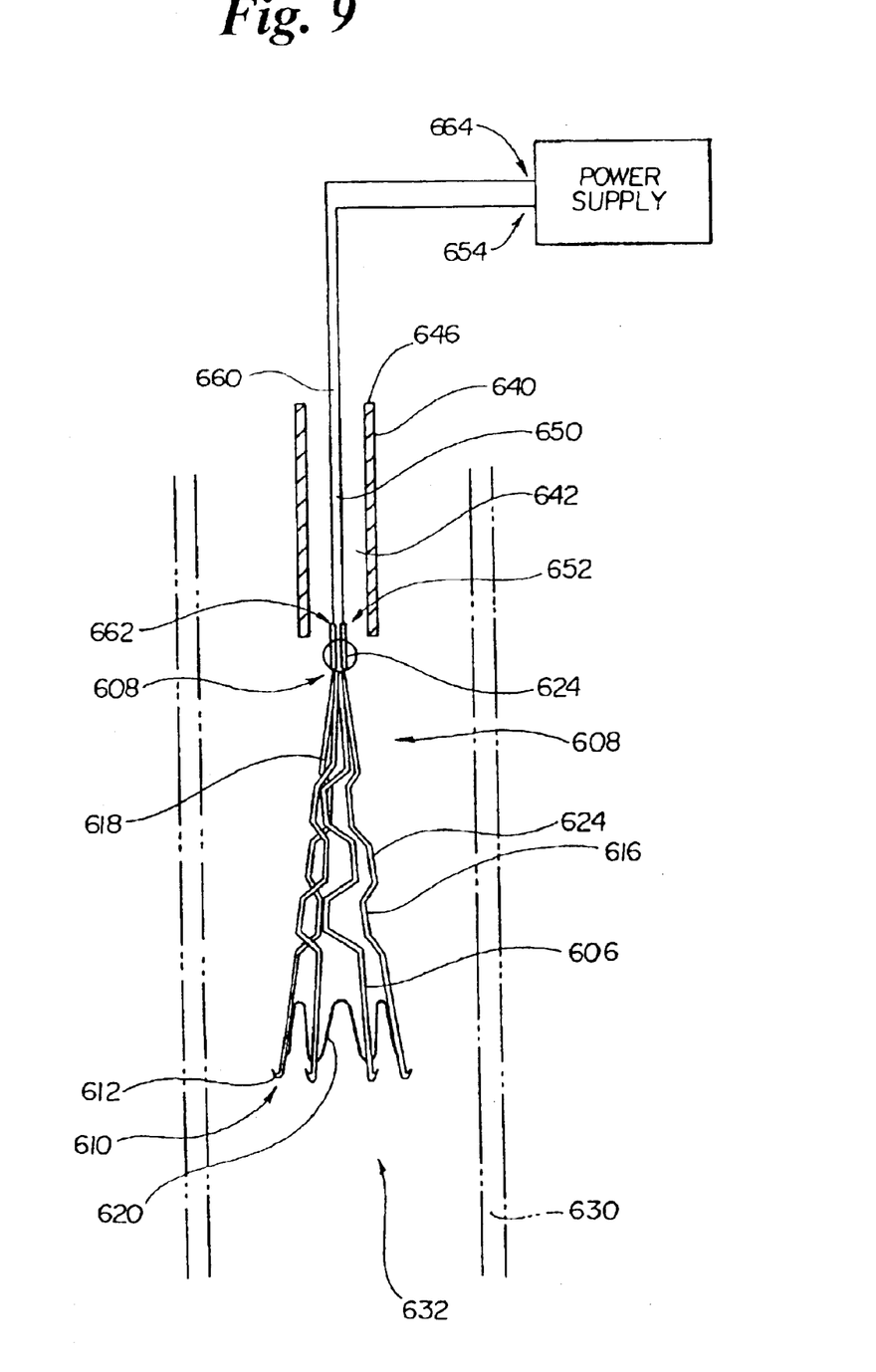
FIG. 9 is a diagrammatic view of the apparatus illustrated in FIG. 8, the thrombus filter being in a contracted state.

FIG. 9, is a diagrammatic view of the thrombus filter of FIG. 8 with ring 620 in a contracted position. As shown in FIG. 9, the contraction of ring 620 causes anchors 612 to disengage the walls of blood vessel 630. Once anchors 612 are disengaged from the walls of blood vessel 630, thrombus filter 600 may be pulled into lumen 642 of removal catheter 640.

Figure 10:
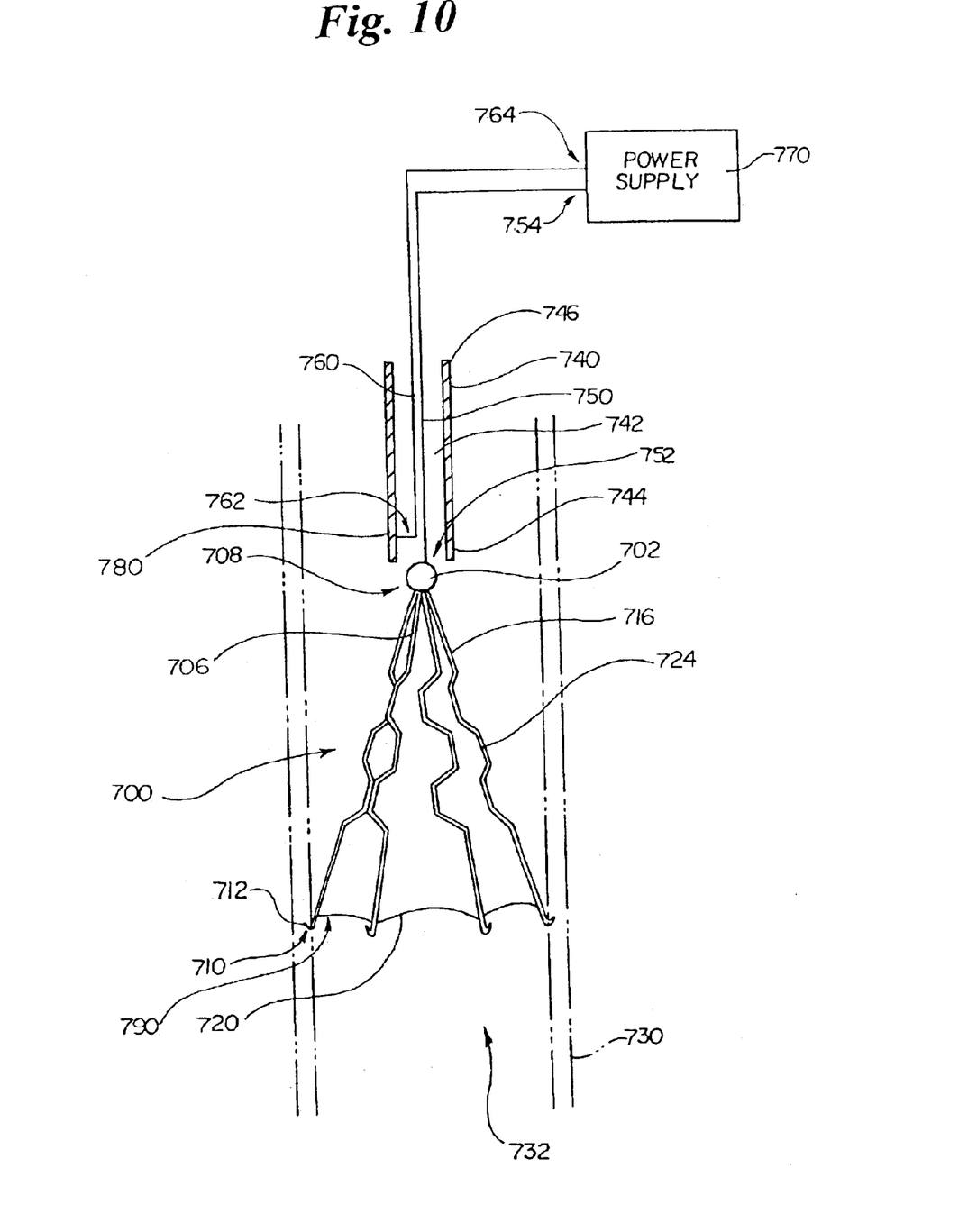
FIG. 10 is a diagrammatic view illustrating an additional process which may be used to remove a thrombus filter from the body of a patient, the diagrammatic view including an exemplary embodiment of a thrombus filter, and an exemplary embodiment of a removal catheter.

FIG. 10 is a diagrammatic view illustrating an additional process which may be used to remove a thrombus filter 700 from the body of a patient. In the embodiment of FIG. 10, thrombus filter 700 includes a body portion 702 and a plurality of spokes 706. Spokes 706 each have a joined end 708 and a free end 710. Joined end 708 of each spoke 706 is fixedly attached to body portion 702. In a presently preferred embodiment, of thrombus filter 700, body portion 702 is electrically insulated from the plurality of spokes 706 with the exception of a first spoke 0.716. In this presently preferred embodiment, body portion 702 is electrically coupled to first spoke 716.

Thrombosis filter 700 also includes a ring 720 which is disposed proximate free ends 710 of spokes 706. In a presently preferred embodiment, ring 720 is electrically coupled to first spoke 716. Also in a presently preferred embodiment, ring 720 is comprised of a shape memory alloy. Suitable shape memory alloys are commercially available from Memry Technologies (Brookfield, Conn.), TiNi Alloy Company (San Leandro, Calif.), and Shape Memory Applications (Sunnyvale, Calif.). In a presently most preferred embodiment, ring 720 is comprised of an alloy of titanium and nickel known in the art as Nitinol.

In FIG. 10, thrombus filter 700 is disposed within a lumen 732 of a blood vessel 730. A removal catheter 740 is also disposed within lumen 732 of blood vessel 730. A distal end 744 of removal catheter 740 is disposed proximate thrombus filter 700. Removal catheter also includes a lumen 742, a proximal end 746, and a ring electrode 780 disposed proximate the distal end thereof.

A first electrical conductor 750 and a second electrical conductor 760 are disposed inside lumen 742 of removal catheter 740. First electrical conductor 750 includes a proximal end 754 and a distal end 752. Second electrical conductor 760 includes a proximal end 764 and a distal end 762.

As shown in FIG. 10, distal end 762 of second electrical conductor 760 is coupled to ring electrode 780. Distal end 752 of first electrical conductor 750 is coupled to body portion 702 of thrombus filter 700. As in the previous embodiment, thrombus filter 700 includes a insulating layer 724.

In the embodiment of FIG. 10, distal end 752 of first electrical conductor 750 has penetrated insulating layer 724 of thrombus filter 700 to form an electrical connection with body portion 702. Also in the embodiment of FIG. 10, insulating layer 724 includes an aperture 790. Aperture 790 allows a portion of thrombus filter 700 to make electrical contact with the body of the patient. Those of skill in the art will appreciate that a number of embodiments of aperture 790 are possible without deviating from the spirit and scope of the present invention.

Proximal end 754 of first electrical conductor 750 and proximal end 764 of second electrical conductor 760 are both electrically coupled to a power supply 770.

Power supply 770 is used to selectively apply a voltage differential between first electrical conductor 750 and second electrical conductor 760.

In the embodiment of FIG. 10, a circuit path between first electrical conductor 750 and second electrical conductor 760 comprises body portion 702, first spoke 716, ring 720, aperture 790, ring electrode 780, and the body of the patient. Those of skill in the art will appreciate that many embodiments of the present invention are possible in which current flows through the body of the patient. For example, current may flow between ring electrode 780 and aperture 790 through the blood. By way of a second example, embodiments of the present invention have been envisioned in which ring electrode 780 is replaced with a conductive patch which may be applied to an area of exposed skin on the patients body. In this envisioned embodiment, the path of current flow through the patient will include tissue.

The voltage differential created by power supply 770 induces a current flow through ring 720. The flow of current through ring 720 causes the temperature of ring 720 to be altered. When the temperature of ring 720 is altered, ring 720 assumes a contracted position as shown in FIG. 11.

Figure 11:
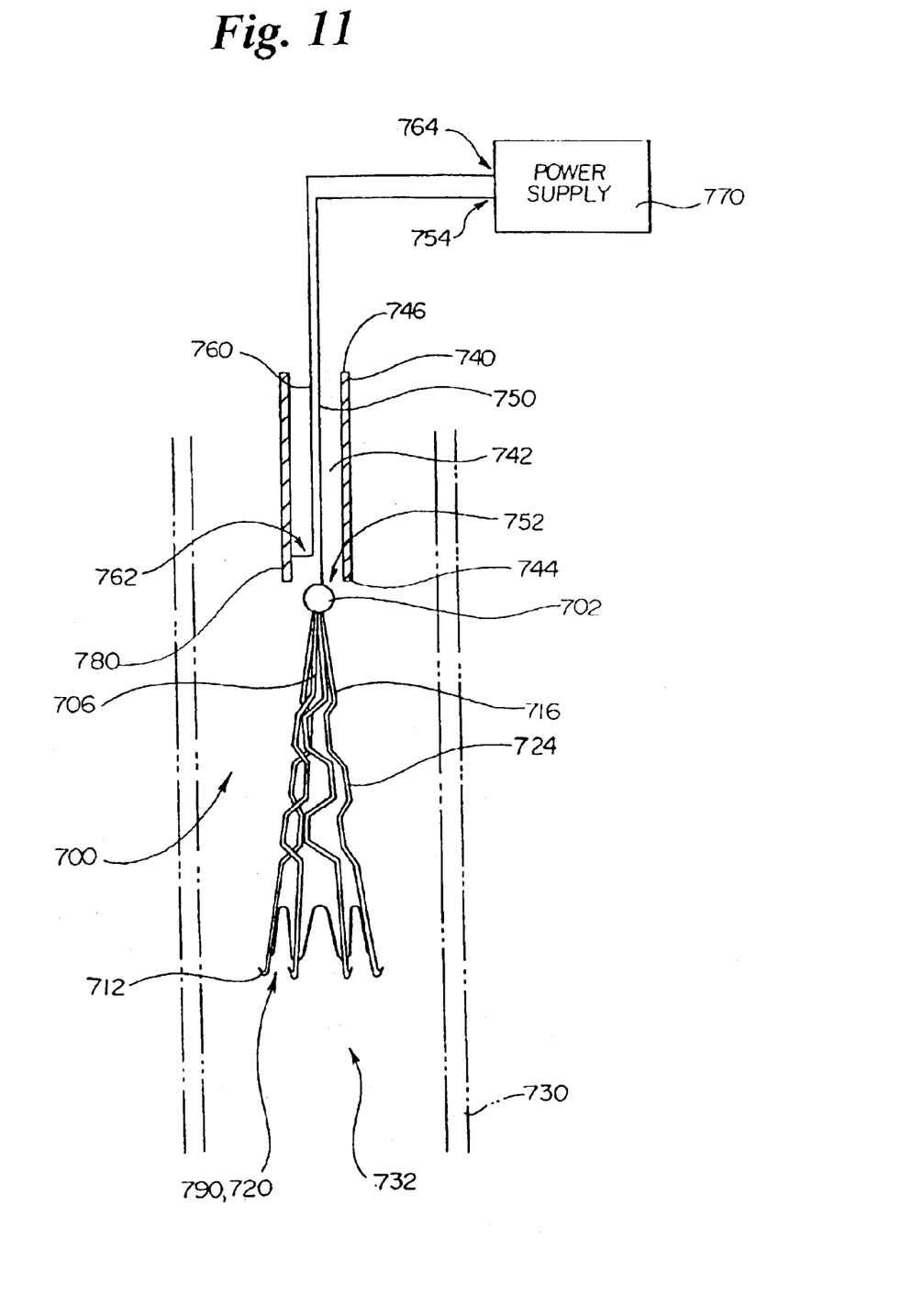
FIG. 11 is a diagrammatic view of the apparatus illustrated in FIG. 10, the thrombus filter being in a contracted state.

FIG. 11, is a diagrammatic view of the thrombus filter of FIG. 10 with ring 720 in a contracted position. As shown in FIG. 11, the contraction of ring 720 causes anchors 712 to disengage the walls of blood vessel 730. Once anchors 712 are disengaged from the walls of blood vessel 730, thrombus filter 700 may be pulled into lumen 742 of removal catheter 740.

Figure 12:
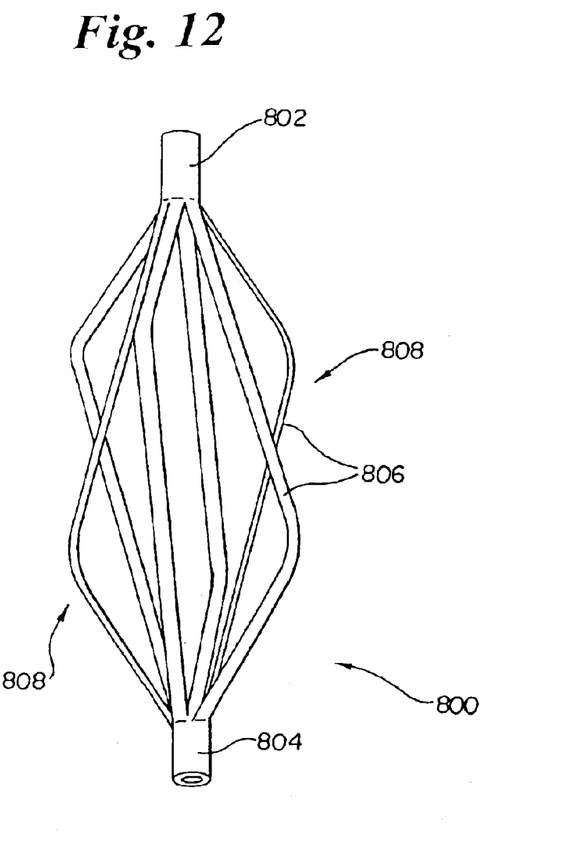
FIG. 12 is a perspective view of an additional embodiment of a thrombosis filter.

FIG. 12 is a perspective view of an additional embodiment of a thrombosis filter 800. Thrombus filter 800 includes a first hub 802, a second hub 804, and a plurality of ribs 806 extending between first hub 802 and second hub 804. In the embodiment of FIG. 12, thrombus filter 800 is shown in an expanded state. When thrombus filter 800 is in an expanded state, each rib 806 forms one or more bends 808.

Figure 13:
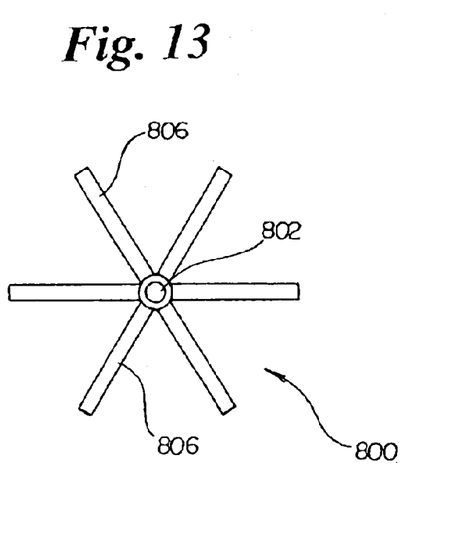
FIG. 13 is a plan view of an additional embodiment of a thrombosis filter.

FIG. 13 is a plan view of thrombosis filter 800 of FIG. 12. First hub 802 and ribs 806 are visible in FIG. 13. In FIG. 13 it may be appreciated that ribs 806 extend radially away from first hub 802 when thrombosis filter 800 is in an expanded state.

Figure 14:
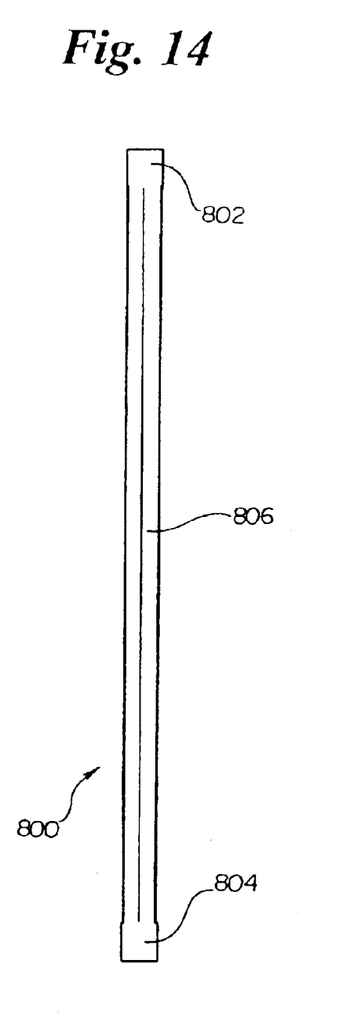
FIG. 14 is a plan view of an additional embodiment of a thrombosis filter.

FIG. 14 is a plan view of thrombosis filter 800 in a contracted state. In FIG. 14 it may be appreciated that ribs 806 are substantially flush with first hub 802 and second hub 804 when thrombosis filter 800 is in a contracted state. Thrombosis filter 800 may be formed by laser cutting a section of tubing to form ribs 806. Methods in accordance with the present invention may be utilized to cause thrombosis filter 800 to contract from the expanded shape shown in FIGS. 12 and 13 to the contracted shape shown in FIG. 14.

Figure 15:
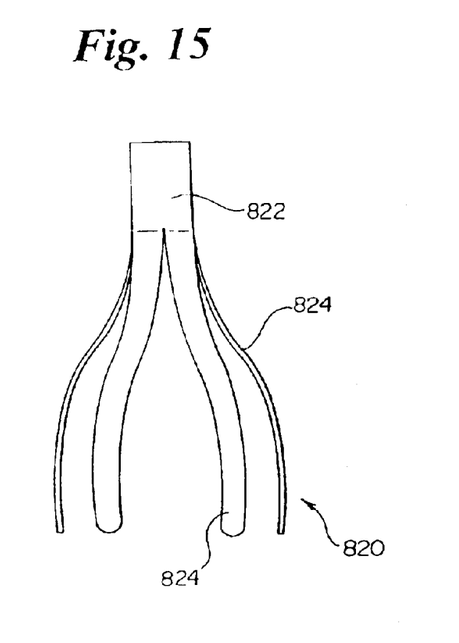
FIG. 15 is a plan view of an additional embodiment of a thrombosis filter; p

FIG. 15 is a plan view of an additional embodiment of a thrombosis filter 820. Thrombosis filter 820 includes a base portion 822 and a plurality of branches 824. In the embodiment of FIG. 15, thrombosis filter 820 is shown in an expanded state. It may be appreciated that branches 824 radiate away from base portion 822 when thrombosis filter 820 is in an expanded state.

Figure 16:
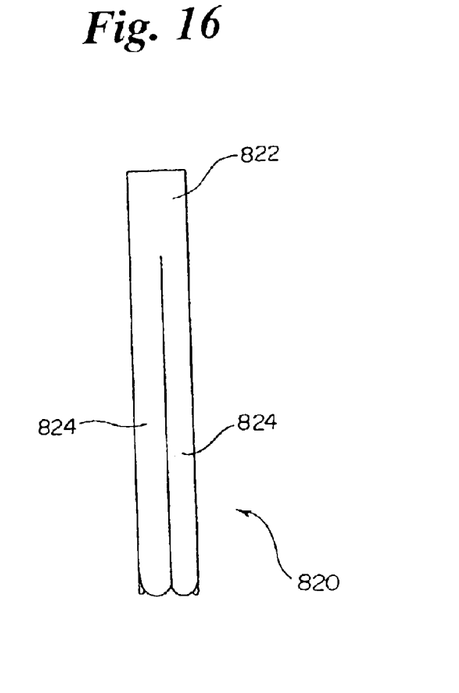
FIG. 16 is a plan view of an additional embodiment of a thrombosis filter; and 5

FIG. 16 is a plan view of thrombosis filter 820 in a contracted state. In FIG. 16 it may be appreciated that branches 824 do not appreciably extend in a radial direction beyond base portion 822 when thrombosis filter 820 is in a contracted state. Methods in accordance with the present invention may be utilized to cause thrombosis filter 820 to contract from the expanded shape shown in FIG. 15 to the contracted shape shown in FIG. 16. Thrombosis filter 820 may be formed by laser cutting a section of tubing to form branches 824.

Figure 17:
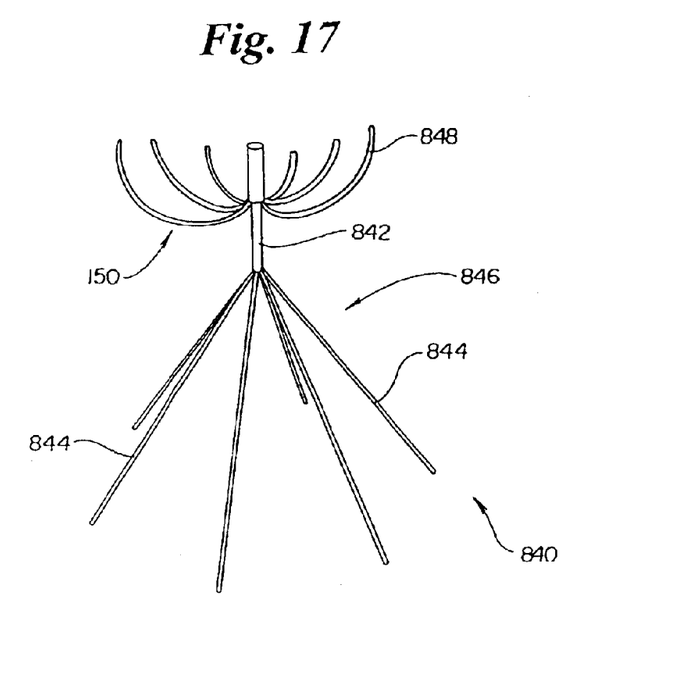
FIG. 17 is a perspective view of an additional embodiment of a thrombosis filter.

FIG. 17 is a perspective view of an additional embodiment of a thrombosis filter 840. Thrombosis filter 840 includes a body portion 842. A plurality of legs 844 radiate away from body portion 842 forming a generally conical portion 846 of thrombosis filter 840. Thrombosis filter 840 also includes a plurality of arms 848. A portion of each arm is fixed to body portion 842. Each arm extends radially away from body portion 842. In the embodiment of FIG. 17 each arm includes a curve 150. In the embodiment of FIG. 17, thrombosis filter 840 is shown in an expanded state. Methods in accordance with the present invention may be utilized to cause thrombosis filter 840 to contract from the expanded shape shown in FIG. 17 to a contracted shape.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of placing a thrombosis filter element within a blood vessel lumen, defined by a blood vessel wall, the method comprising steps of:

providing a thrombosis filter having a plurality of struts, wherein a portion of the struts comprise a shape-memory material, the struts comprising the shape-memory material capable of modifying their preexisting configuration by altering the temperature of said material, the struts each having a free end and an anchor proximate each free end;

advancing the thrombosis filter along said vessel lumen of the patient until the thrombosis filter is disposed in the selected portion of the vessel lumen;

providing a means for inducing a current in the shape-memory material; and altering the temperature of the shape-memory material with the current resulting in the struts extending to engage the anchors with the vessel wall.

2. The method according to claim 1, wherein the means for inducing a current in the shape-memory material is an electrode.

3. The method according to claim 1, wherein the current is heat.

* * * * *